United States Patent
Scholl et al.

(10) Patent No.: US 6,175,754 B1
(45) Date of Patent: *Jan. 16, 2001

(54) METHOD AND APPARATUS FOR MEASURING CORNEAL INCISIONS

(75) Inventors: John Anthony Scholl, Danville; Thomas A. Silvestrini, Alamo; Isidro Matias Gandionco, Fremont, all of CA (US); William P. Kuhn, Tucson, AZ (US); Phillip C. Baker, Orinda, CA (US)

(73) Assignee: KeraVision, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/476,462

(22) Filed: Jun. 7, 1995

(51) Int. Cl.$^7$ .................................................... A61B 17/00

(52) U.S. Cl. ................................................ 600/407; 606/4

(58) Field of Search ................................ 128/653.1, 898, 128/897, 660.01, 660.06; 606/4, 5, 6, 2, 11, 107, 166, 3; 623/4, 5; 600/407, 437, 442

(56) References Cited

U.S. PATENT DOCUMENTS

| | | |
|---|---|---|
| 4,423,728 | 1/1984 | Lieberman . |
| 4,429,696 | 2/1984 | Hanna . |
| 4,452,235 | 6/1984 | Reynolds . |
| 4,564,018 | 1/1986 | Hutchinson et al. . |

(List continued on next page.)

FOREIGN PATENT DOCUMENTS

| | | |
|---|---|---|
| 2144537 | 3/1985 | (GB) . |
| 92/19930 | 11/1992 | (WO) . |

OTHER PUBLICATIONS

Molesini et al., "Focus–Wavelength Encoded Optical Profilometer," *Optics Communications* 49(4): 229–233 (1984).

Maly et al., "Real–Time Stereoscopic Confocal Reflection Microscopy Using Objective Lenses with Linear Longitudinal Chromatic Dispersion," *Scanning* 16(3): 187–192 (1994).

*Primary Examiner*—Marvin M. Lateef
*Assistant Examiner*—Shawna J. Shaw
(74) *Attorney, Agent, or Firm*—Harry Macey; KeraVision, Inc.

(57) ABSTRACT

A method and apparatus for performing a surgical procedure on a patient is described. An incision is made into tissue of the patient to create a tissue pocket. The tissue has an anterior surface. Preferably, the tissue is corneal tissue of an eye. A reflective element is inserted into the pocket. An energy source generates a radiant energy signal, which is directed toward the reflective element. Reflected energy is received from the reflective element. A detector determines the depth of the reflective element below the anterior surface based upon the energy reflected by the reflective element. The speed of transmission of the radiant energy in the reflective element is different (preferably slower) than the speed of transmission of the radiant energy in the tissue. The reflective element may be in the form of a tool on which is disposed a biocompatible polymer layer, the layer comprising trapped air spaces, or a tool having an open space for containing trapped air. The radiant energy may take the form of ultrasound generated by an ultrasonic probe, or light generated by a confocal microscope. The confocal microscope may employ longitudinal chromatic aberration to measure the depth of the reflective element. When employing a confocal microscope, the depth of the reflective element is a function of the reflected energy from the anterior surface and the reflected energy from the reflective element.

16 Claims, 11 Drawing Sheets

U.S. PATENT DOCUMENTS

| | | |
|---|---|---|
| 4,598,714 | 7/1986 | Kremer et al. . |
| 4,671,276 | 6/1987 | Reynolds . |
| 4,688,570 | 8/1987 | Kramer et al. . |
| 4,705,037 | 11/1987 | Peyman et al. . |
| 4,813,435 | 3/1989 | Arms . |
| 4,815,463 | 3/1989 | Hanna . |
| 4,829,251 | 5/1989 | Fischer . |
| 4,844,617 | 7/1989 | Kelderman et al. . |
| 4,881,808 | 11/1989 | Bille et al. . |
| 4,887,592 | 12/1989 | Loertscher . |
| 4,941,093 | 7/1990 | Marshall et al. . |
| 4,964,862 | 10/1990 | Arms . |
| 4,965,441 | 10/1990 | Picard . |
| 4,993,428 | 2/1991 | Arms . |
| 4,997,437 | 3/1991 | Grieshaber . |
| 5,063,942 | 11/1991 | Kilmer et al. . |
| 5,083,220 | 1/1992 | Hill . |
| 5,084,612 | 1/1992 | Iwasaki et al. . |
| 5,090,955 | 2/1992 | Simon . |
| 5,109,276 | 4/1992 | Nudelman et al. . |
| 5,117,466 | 5/1992 | Buican et al. . |
| 5,120,953 | 6/1992 | Harris . |
| 5,161,052 | 11/1992 | Hill . |
| 5,192,980 | 3/1993 | Dixon et al. . |
| 5,194,918 | 3/1993 | Kino et al. . |
| 5,196,006 | 3/1993 | Klopotek et al. . |
| 5,200,819 | 4/1993 | Nudelman et al. . |
| 5,200,838 | 4/1993 | Nudelman et al. . |
| 5,208,648 | 5/1993 | Batchelder et al. . |
| 5,215,104 | * 6/1993 | Steinert . |
| 5,220,403 | 6/1993 | Batchelder et al. . |
| 5,225,678 | 7/1993 | Messerschmidt . |
| 5,241,364 | 8/1993 | Kimura . |
| 5,260,569 | 11/1993 | Kimura . |
| 5,283,433 | 2/1994 | Tsien . |
| 5,293,870 | * 3/1994 | Ophir et al. . |
| 5,296,700 | 3/1994 | Kumagai . |
| 5,296,703 | 3/1994 | Tsien . |
| 5,306,902 | 4/1994 | Goodman . |
| 5,307,203 | 4/1994 | Hill . |
| 5,308,355 | * 5/1994 | Dybbs . |
| 5,311,021 | 5/1994 | Messerschmidt . |
| 5,318,047 | 6/1994 | Davenport et al. . |
| 5,329,352 | 7/1994 | Jacobsen . |
| 5,355,252 | 10/1994 | Haraguchi . |
| 5,437,657 | * 8/1995 | Epstein . |
| 5,497,147 | 3/1996 | Arms et al. . |
| 5,560,356 | * 10/1996 | Peyman . |
| 5,601,584 | * 2/1997 | Obagi et al. . |
| 5,611,805 | * 3/1997 | Hall . |
| 5,651,782 | * 7/1997 | Simon et al. . |
| 5,653,725 | * 8/1997 | Simon et al. . |
| 5,662,668 | * 9/1997 | Kurwa . |
| 5,772,970 | * 3/1998 | Colvard et al. . |
| 5,984,914 | * 11/1999 | Cumming ................................ 606/4 |
| 5,988,824 | * 11/1999 | Rowsey, Jr. ......................... 359/882 |

* cited by examiner

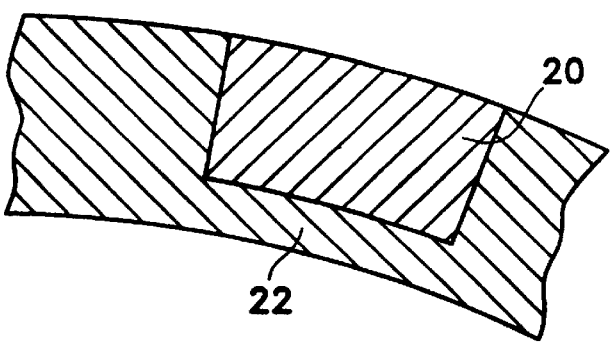
Fig. 2
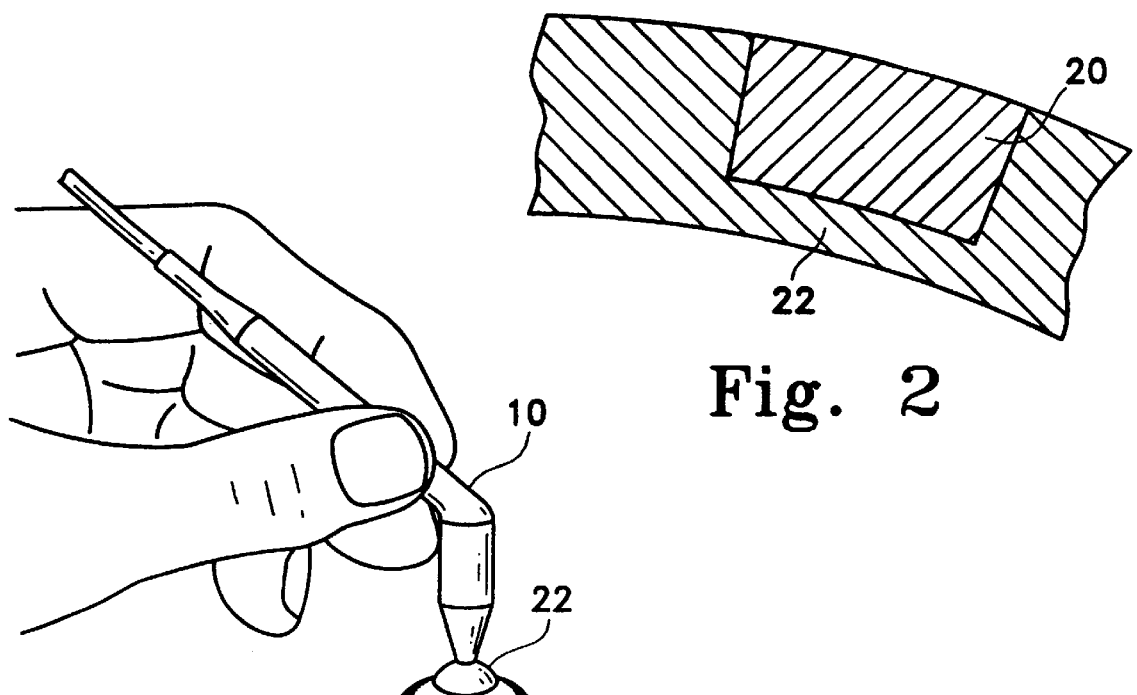
Fig. 1
Fig. 4
Fig. 3

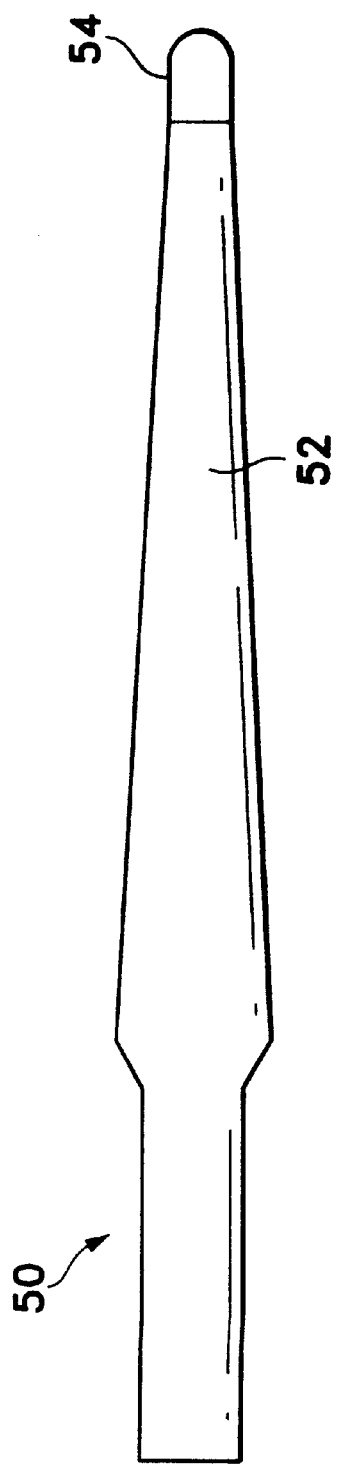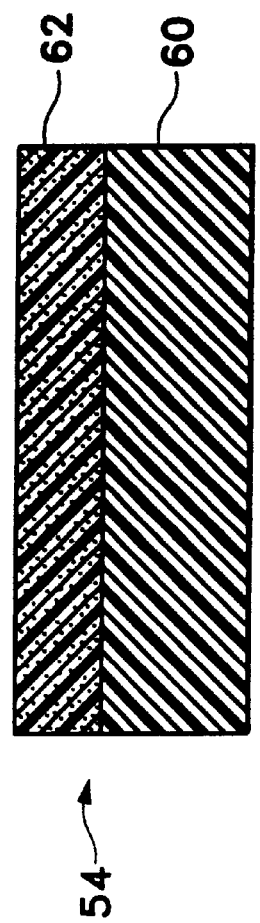
Fig. 5
Fig. 6

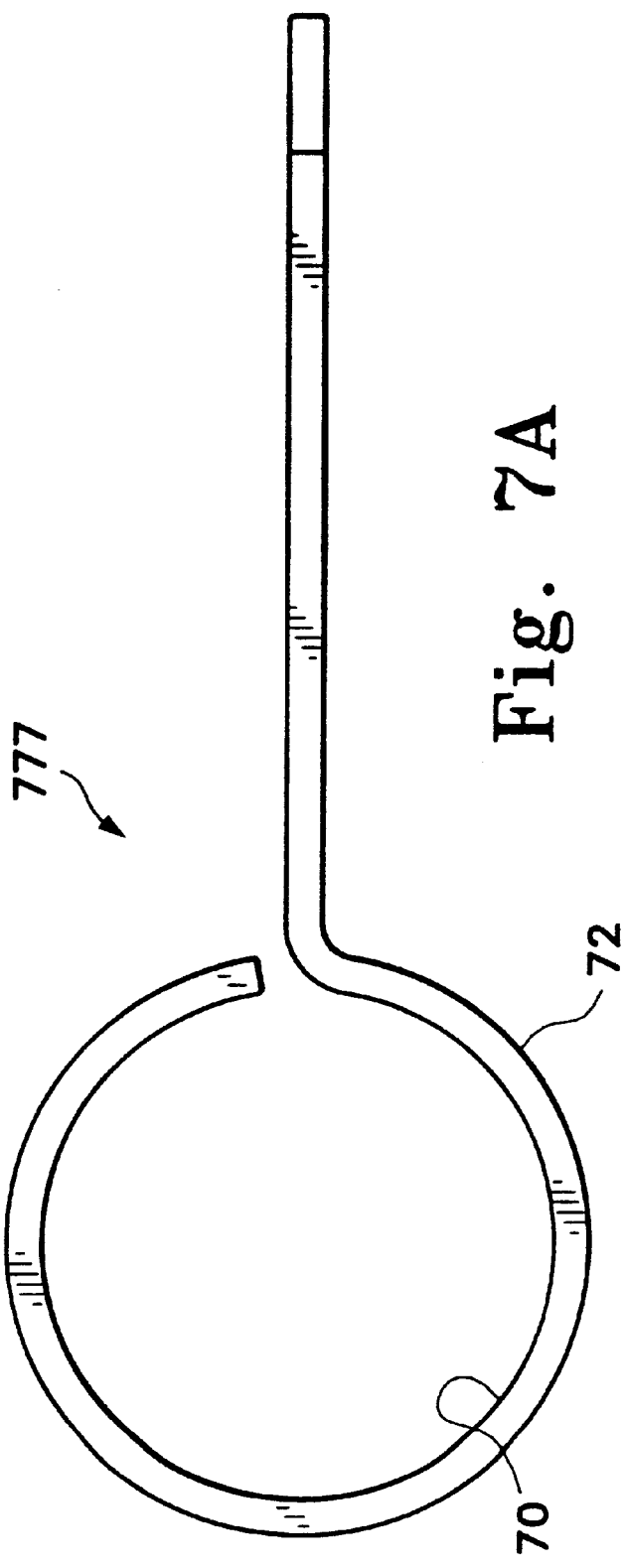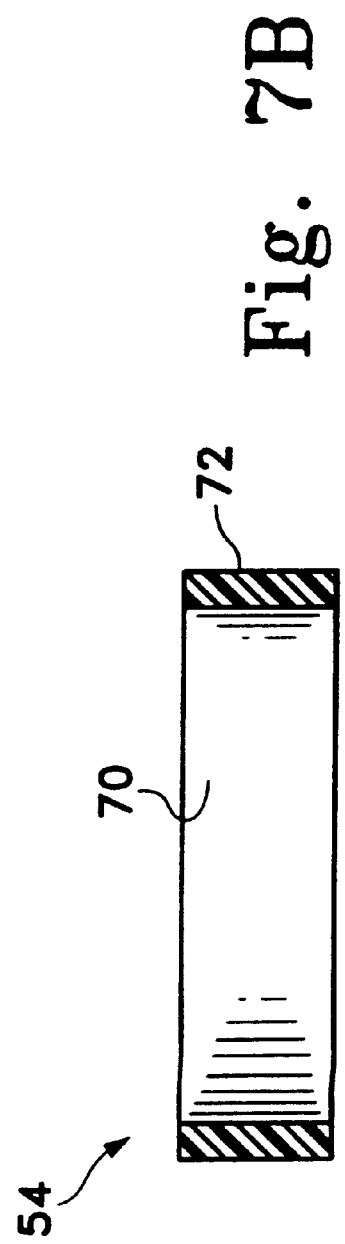

METHOD AND APPARATUS FOR MEASURING CORNEAL INCISIONS

BACKGROUND OF THE INVENTION

This invention relates to the field of eye surgery, and in particular to a method and apparatus for measuring the depth of an incision or pocket in a patient's cornea.

Some surgical procedures for the correction of visual disorders require incisions in the patient's cornea. For example, U.S. Pat. No. 4,452,235 describes a method and apparatus for corneal curvature adjustment. The method involves insertion of one end of a split-end Intrastromal Corneal Ring (ICR) into an incision formed in the patient's cornea and movement of the ring in a circular path until the ends of the ring meet. The ICR's thickness relates to the degree of corneal flattening that can be obtained, to provide for correction of varying degrees of myopia. ICRs are made by Keravision, Inc. and are further discussed in U.S. Pat. No. 5,318,047, entitled METHOD FOR CORNEAL CURVATURE VARIATION, and issued to Davenport et al. on Jun. 7, 1994, which is hereby incorporated by reference. Similarly, U.S. Pat. No. 5,090,955 describes the adjustment of corneal curvature through the injection of a polymeric gel into an incision made in a patient's cornea.

Both of these corrective procedures require precise measurement of the depth of the pocket into which the gel or ICR is to be inserted. Both procedures require an initial measurement of the corneal thickness, typically employing an ultrasonic pachymeter. An adjustable-depth diamond knife then makes a peripheral incision to a depth that corresponds to a predetermined fraction of the pachymetry measurement at the incision's side. For example, to insert an ICR, the incision depth corresponds to 68% of the pachymetry measurement.

After the initial incision is made, at least one lamellar pocket is formed for insertion of the gel or ICR. Using conventional technology, the depth of the pocket is estimated using a set of mechanical corneal thickness gauges, such as those manufactured by KeraVision, Inc., the assignee of the present invention. These gauges feature gaps of different widths for measuring corneal tissue thickness, and thereby pocket depth. If the measurement indicates that the pocket is not deep enough into the corneal stroma, the diamond knife is used to make a slightly deeper incision in order to create a second pocket at a deeper level. This procedure is repeated until a corneal pocket of a desired depth is created. After the pocket is finally created, the pocket is further formed into a annular shape for injection of a polymeric gel or an ICR.

Measuring the depth of the corneal pocket is a critical step in ICR implantation and other corneal surgery procedures. The depth must be measured accurately since the depth of the implant can affect the resulting refractive change. Therefore, it is desirable to provide an accurate and dependable way of measuring the depth of corneal pockets that are used for refractive correction and other ocular surgery procedures.

SUMMARY OF THE INVENTION

The present invention provides a method and apparatus for measuring the depth of a pocket made in tissue. A controlled-depth incision is made into the tissue of a patient and the tissue is delaminated at the bottom of the incision to create a tissue pocket. The tissue has an anterior surface. Preferably, the tissue is the corneal tissue of an eye. A reflective element is inserted into the pocket. An energy source generates a radiant energy signal, which is directed toward the reflective element. Reflected energy is received from the reflective element. A detector determines the depth of the reflective element below the anterior surface based upon the energy reflected by the reflective element.

The speed of transmission of the radiant energy in the reflective element is different from the speed of transmission of the radiant energy in the tissue. Preferably, the speed of transmission in the reflective element is slower than the speed of transmission in the tissue. For optical reflection, the reflective element may have either a substantially different refractive index or a substantially higher reflectivity than the tissue being measured.

The reflective element may be in the form of a tool on which is disposed a biocompatible polymer layer, the layer comprising trapped air spaces. Alternatively, the reflective element may be a tool having an open space for containing trapped air.

The radiant energy may take the form of ultrasound generated by an ultrasonic probe, or light generated by a confocal microscope. The confocal microscope may employ longitudinal chromatic aberration to measure the depth of the reflective element. When a confocal microscope is used, the depth of the reflective element is a function of the reflected energy from the anterior surface and the reflected energy from the reflective element.

BRIEF DESCRIPTION OF THE DRAWINGS

The objects, features and advantages of the present invention will be apparent to one skilled in the art in light of the following detailed description in which:

FIG. 1 is a schematic perspective view of an ultrasonic pachymeter probe for measuring corneal thickness in accordance with the invention.

FIG. 2 is a schematic cross-sectional view of an incision formed in accordance with the invention.

FIG. 3 is a schematic elevational view showing the incision of the cornea in accordance with the invention.

FIG. 4 is a schematic cross-sectional view of a tool for measuring pocket depth in accordance with the invention.

FIG. 5 illustrates a reflective tool in accordance with the present invention.

FIG. 6 illustrates a cross-sectional view of the tool blade according to one embodiment of the present invention.

FIGS. 7A and 7B illustrate top and cross-sectional views of the reflective tool blade according to another embodiment of the present invention.

DETAILED DESCRIPTION OF THE INVENTION

Figure 8:
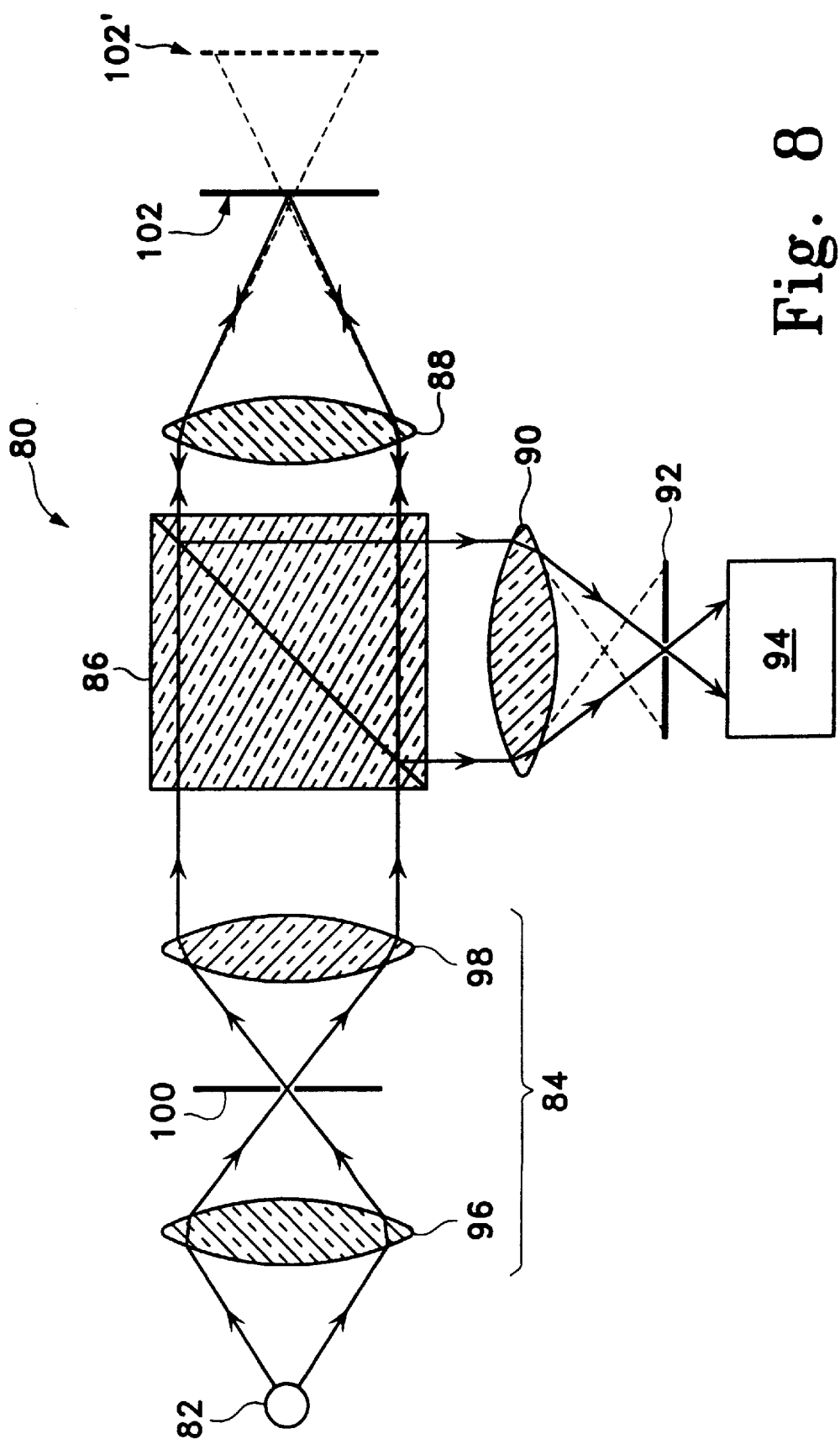
FIG. 8 illustrates a confocal microscope.

The present invention relates to a method and apparatus for determining the depth of an incision or pocket in a patient's cornea. According to the present invention, a signal is directed and transmitted into the cornea. The transmitted energy may be ultrasonic, optical/electromagnetic or any other energy that is capable of being reflected without causing damage to the tissue being measured. A reflective boundary is established in a corneal pocket by inserting air and/or an object into the pocket. Echo information from the reflection of the energy by the tissue/air or tissue/object interface is detected and analyzed to calculate the depth of the pocket.

FIGS. 1–4 illustrate some of the steps of a corneal surgery procedure, specifically, preparation of a patient's cornea for the implementation of an ICR. Those skilled in the art will recognize that the present invention may be employed to measure tissue pockets in a wide variety of surgical procedures, including automated lamellar keratotomy, suture cataract incisions, or any procedure to implant an inlay into the eye.

Prior to the initial incision, an ultrasonic pachymetry probe 10 is placed against the cornea 22 of the patient's eyeball 12 as shown in FIG. 1 to measure the thickness of the cornea. Alternatively, the corneal thickness can be measured using the confocal microscopes described below. As shown schematically in FIGS. 2 and 3, an incision 20 is made in the cornea using a diamond blade knife 16. The depth is preferably in the range of 0.30–0.45 mm and the incision length is preferably between 1–2 mm, although these dimensions may vary depending upon the circumstances of the procedure.

A tool or glide 26 is inserted in the incision as shown in FIG. 4 to separate the lamella at the base of the incision. The glide is moved parallel to the anterior surface of the cornea to form an initial pocket 30 within the cornea at the base of the incision.

Prior to the formation of the complete annular track for an ICR or other corneal implant, it is desirable to determine whether the initial pocket is at the correct depth. Standard measurement systems, such as ultrasonic pachymeters, are designed to detect the interface between the posterior surface of the cornea and the anterior chamber immediately behind the cornea. The pachymeter detects a reflection at this interface that is caused by a mismatch of the speed of sound conduction through the different media of the anterior chamber and the cornea. The present invention provides a means not just for measuring the full thickness of a cornea, but the depth of a pocket made at a partial depth of the cornea.

Three techniques for measuring pocket depth based upon a reflected energy signal are described herein. The first technique is based upon ultrasonic pachymetry. The second and third techniques rely upon confocal microscopes.

As for the ultrasonic technique, pocket depth can be measured without modifying the signal processing subsystem of a conventional ultrasonic pachymetry apparatus, which itself is known to those of ordinary skill in the art. The ultrasonic pachymetry system can be used to detect the interface between corneal tissue and a material inserted into the corneal pocket, provided that the material conducts sound at a different rate than the corneal tissue. By using a material that conducts sound slower than corneal tissue, the pachymeter will not have to be adjusted to detect the interface. One such material is air. The pachymeter will display as its output the depth of the pocket where the material is placed, and not the thickness of the patient's cornea.

To use the pachymetry system to measure the depth of the pocket or incision, air and/or another material must be placed in the pocket or at the bottom of the incision to form an ultrasonically reflective boundary. In several embodiments of this invention, a special tool is used to introduce air into the pocket or incision. FIG. 5 illustrates a reflective tool 50, which includes a shank 52 and a blade 54. Preferably, the blade 54 is bent out of the page at an angle ranging from 40–80 degrees with respect to the shank 52. Unlike prior art glide tools or spatulas, the tool of this invention has a surface containing one or more air pockets.

FIG. 6 illustrates a cross-sectional view of the blade 54. As shown in FIG. 6, the blade 54 includes a glide body portion 60, on which is disposed a biocompatible polymer foam layer 62. The layer 62 is composed primarily of trapped air spaces. Materials such as ePTFE, polyurethane, PVC, PP, PE, or polystyrene may be used to form the layer 62, although any porous and hydrophobic biocompatible material may be used. The preferred thickness of the layer 62 is in the range of 0.003 to 0.020 inches. The thickness of the blade portion 60 is preferably in the range of 0.003 to 0.007 inches. The shank is approximately 0.012±0.006 inches thick. The tool body 60 itself can be formed from a thermal plastic polymer or any other suitable stiff material.

Alternatively, as shown in FIGS. 7A and 7B, the tool may comprise a spatula type device 777 having a hole 70 formed by a distal end loop portion 72 of the tool. The tool, when inserted into a corneal pocket, maintains an open space between opposing layers of the cornea. The air trapped in the hole 70 provides a reflective boundary for the ultrasonic signal. In practice, the field around the tool is dry enough so that the hole does not fill up with fluid, which would hinder or obviate reflection. In one embodiment, a thin tube or cannula can be run through the tool body from the hole 70 to the handle of the tool so that fluid may be suctioned out of the hole 70. Those skilled in the art will understand that the present invention may be formed by modifying a wide variety of tools used in corneal surgery, and is not limited to the tool shapes disclosed herein.

It should be noted that the incision depth measurement method of this invention will work with prior art insertion tools, such as the insertion spatula disclosed in U.S. Pat. No. 5,090,955. In addition, in place of inserting a tool such as the modified glide blade into the incision to create an ultrasonically reflective boundary, air may be injected into the pocket prior to the pachymetry reading or a polymer foam strip may be inserted into the pocket with a metal pick or spatula.

One drawback of ultrasonic pachymetry is that the acoustic energy from the ultrasonic probe cannot be efficiently coupled from the probe to the cornea through air. Thus, the probe must touch the eye to measure the thickness of the corneal pocket to achieve a reasonable degree of resolution. This requires that the probe be sterilized. Further, any procedure that requires contact with the eye distorts the surface of the eye somewhat, which could affect the depth measurement.

A technique for measuring distances in corneal tissue that does not require contact with the eye is disclosed in "Distance Measuring Confocal Microscope," U.S. patent No. application Ser. No. 08/484,204, filed concurrently herewith and assigned to the assignee of the present invention. That application is fully incorporated by reference herein. Confocal microscopy is a highly accurate means of obtaining high resolution images in both lateral dimension and in depth. In typical confocal microscopy, a monochromatic point source of light is projected onto a surface and a portion of the reflected light is separated and then imaged onto a pinhole. The amount of light through the pinhole is measured by a detector.

FIG. 8 depicts a conventional confocal microscope that may be used to determine depth and surface topology. Confocal microscope 80 comprises a light source 82, input optics 84, beam splitter 86, objective lens 88, output lens 90, pinhole aperture 92, and detector 94. Light from source 82 is first collimated by input optics 84, which itself consists of condenser lens 96 and collimating lens 98, and input pinhole aperture 100. Once collimated, the light passes through beam splitter 86 and is focused onto target 102 by objective lens 88. A portion of the light reflected by target 102 is again reflected by beam splitter 86 and focused onto pinhole aperture 92 by output lens 90. The quantity of light passing through pinhole 92 is then measured by detector 94.

Also shown in FIG. 8 is the manner in which confocal microscope 80 determines depth. Depicted in dotted line is target 102' that is not at the focus of objective lens 88. The reflected light from target 102' also in dotted line, is dispersed more widely than the reflected light 102 when it reaches pinhole aperture 92. As a result, the intensity of the light reaching detector 94 after passing through aperture 92 is diminished for out-of-focus targets. This signal can be used to control the positioning of the microscope until a maximum signal is returned, at which point the microscope position corresponds to the distance from the target.

The lateral resolution of a confocal microscope is better than that of a normal microscope. Since only the point of interest is illuminated, scattered light is greatly reduced. Additionally, very high resolution in depth is obtained since the returned signal falls off very rapidly as the surface is moved away from the plane of best focus.

The confocal microscope can be used to measure the depth of a corneal pocket by inserting a material into the pocket that has a different refractive index than that of the surrounding corneal tissue. The principal is similar to ultrasonic pachymetry in that the refractive index is a measure of the velocity of light in a medium, and light is reflected at the interface between two media in which light travels at different speeds.

The same reflective tools and materials, including air, that were used for ultrasonic pachymetry, as described above, can be used to measure corneal pocket depth with a confocal microscope. In addition, metal or plastic may be employed to form the reflective boundary. In general, any material that exhibits a significant difference in refractive index, approximately on the order of $10^{-3}$, from the surrounding corneal tissue may be employed. In addition, any material that exhibits a substantially higher reflectivity than the tissue being measured may be employed.

In order to measure the depth of the corneal pocket, and thus the depth of the reflective tool or material, the confocal microscope must focus over a range of depths throughout the cornea to determine the distance at which peak reflection occurs. To vary the focus, the lenses must be mechanically moved to detect reflections at different focal points. In measuring corneal pocket depth, a first peak will occur at the interface between the anterior surface of the cornea and the ambient environment, and a second peak will be measured at the reflective boundary formed by the reflective tool or material. However, during the time in which the focus is varied, the corneal thickness may vary somewhat due to the movement of the eye muscle and blood pumping through the capillaries of surrounding eye tissues.

Accordingly, the patent application "Distance Measuring Confocal Microscope" discloses a confocal microscope that incorporates longitudinal chromatic aberration ("LCA") into the objective lens in order to measure depth. The LCA confocal microscope reflects a polychromatic light beam off of a target object. Because of the longitudinal chromatic aberration of the objective lens, different wavelengths are focused at different points along the axis of the lens. As a result, peaks in the intensity of the reflected light at different wavelengths correspond to distances of different reflective surfaces. Thus, by measuring the spectrum of the returned light (instead of just overall intensity), the distance of the reflecting surfaces can be determined. Further, because the LCA technique measures a range of distances simultaneously due to the spatial spreading of the light beams at different wavelengths, pocket depth can be measured with no motion of the LCA confocal microscope.

Several embodiments of confocal microscopes made in accordance with the principles of the invention will now be presented.

FIRST LCA EMBODIMENT

Figure 9A:
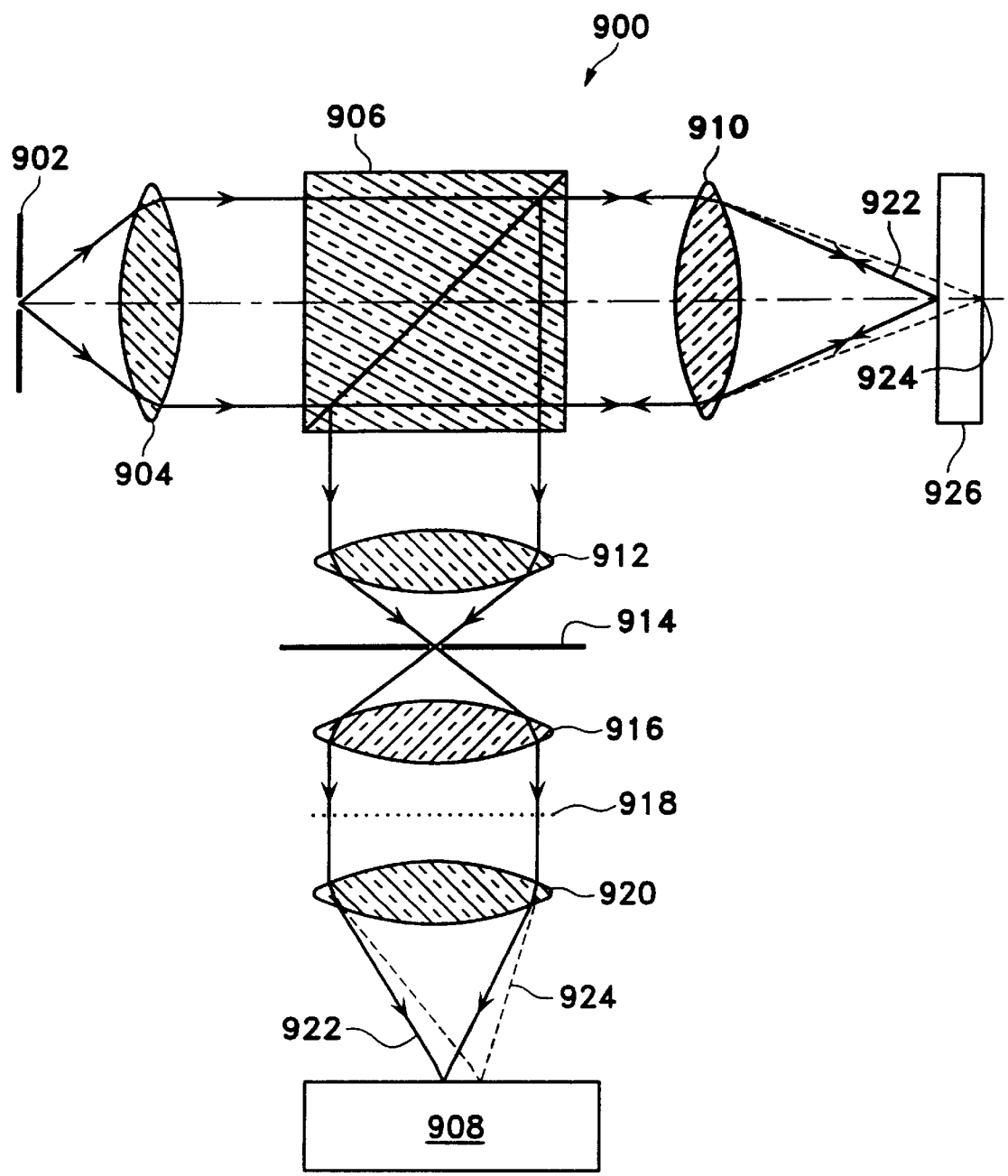
FIGS. 9A and 9B illustrate a first embodiment of a distance-measuring confocal microscope that employs longitudinal chromatic aberration (LCA).

FIG. 9A illustrates a first embodiment 900 of a non-mechanical, distance-measuring confocal microscope made in accordance with the principles of the present invention. This embodiment comprises pinhole light source 902 (e.g., source 82 and condenser lens 96 of FIG. 8), first collimator 904, beam splitter 906, spectrometer 908, first objective lens 910, second objective lens 912, pinhole aperture 914, second collimator 916, grating 918, and imaging lens 920.

In operation, system 900 emits a polychromatic light from pinhole source 902. Light source 902 may be comprised of one or more lasers or a broadband source, such as white light. However constructed, the only requirement is that light source 902 emit more than one wavelength so that depth distance may be determined by the spectral spread of reflected light. This light, collimated by lens 904, is transmitted through beamsplitter 906. About half of the incident light is lost principally by reflection out of the top by beamsplitter 906, and by scattering or the like, while the other half of this light passes through first objective lens 910.

Objective lens 910 is constructed with a known amount of longitudinal chromatic aberration. Thus, the incident light beam spreads out longitudinally according to wavelength. As represented in FIG. 9A, the incident beam focuses its shortest wavelength according to a solid beam 922 and its longest wavelength according to a dotted beam 924. For the purposes of illustration, an object 926 is conveniently placed in this figure having a first surface located at the focal point of beam 922 and a second surface at the focal point of beam 924. As these surfaces are at the focal point of these two beams, most of the light from these two beams will be collected and detected; while other beams (i.e., other wavelengths) will be filtered by pinhole aperture 54 and largely attenuated at the detector 908. Those skilled in the art will recognize that the LCA range should preferably be longer than the maximum thickness of the object.

The reflected light retraces the same optical path backwards—collimated by objective lens 910, until the reflected light impinges upon beamsplitter 906. At beamsplitter 906, approximately half of this reflected light is redirected downward to second objective lens 912. Second objective lens 912 is designed to have very little or no longitudinal chromatic aberration. Pinhole aperture 914 is advantageously positioned at the focal point of second objective lens 912. Thus, any collimated light, regardless of wavelength, is focused by lens 912 onto pinhole aperture 914 and passed along to a detector stage.

Other wavelengths of light that are not collimated by objective lens 910 do not focus precisely onto pinhole aperture 914. Thus, the intensity of these other wavelengths is greatly attenuated. In effect, pinhole aperture 914 acts as a filter. As will be discussed below, this unique arrangement allows for the resolution of very close distances between reflective surfaces on objects, such as object 926.

The wavelengths that pass through aperture 914 are once again collimated by lens 916 to be spatially dispersed by grating 918 according to wavelength. Imaging lens 920 focuses these dispersed beams 922 and 924 onto spectrometer 908 where these wavelengths (and their intensities) are recorded. If the response of the spectrometer is normalized by the source spectrum, then the peak wavelength in the spectrum will correspond to a specific position of the object relative to the objective lens. This permits the depth to be determined without the need to mechanically control the spacing between the objective lens and object.

Figure 9B:
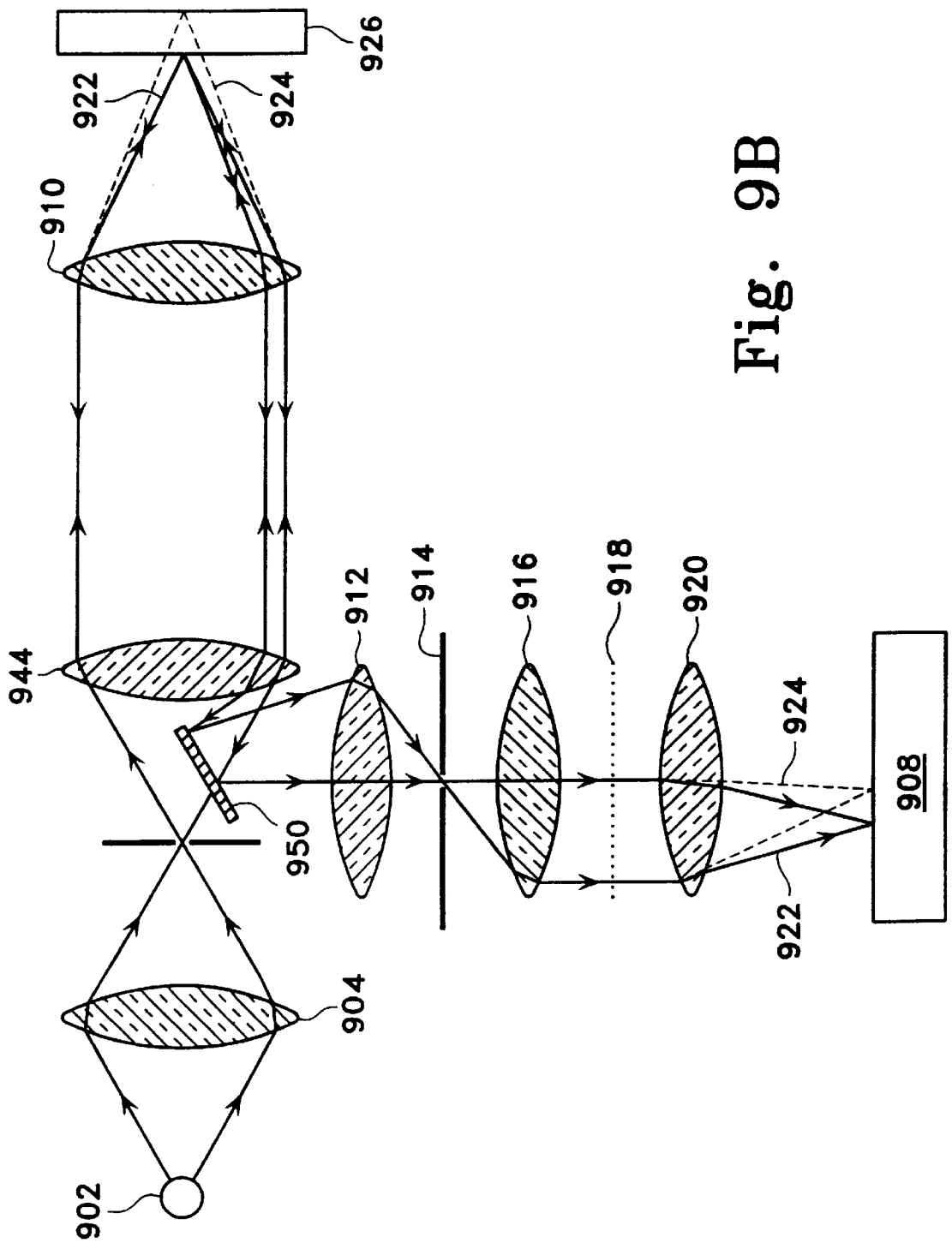

A variation of the first embodiment is depicted in FIG. 9B. The main difference between FIG. 9A and FIG. 9B is the addition of mirror 950 in FIG. 9B. One advantage of the addition of mirror 950 is the elimination of the need of beamsplitter 906 in FIG. 9A. As can be seen, with mirror 950 placed in the optical path as situated, approximately one half of the polychromatic beam passes through lens 944 and impinges onto object 926. The longitudinal spread of beams still impinges on object 926 in the same manner as in FIG. 9A; however, on the return reflection, approximately one half of the reflected light is intercepted and reflected downward by mirror 950. The path of the reflected light passes through the same optical elements as before in FIG. 9A, culminating in a lateral spread of beams at detector 908.

SECOND LCA EMBODIMENT

Figure 10:
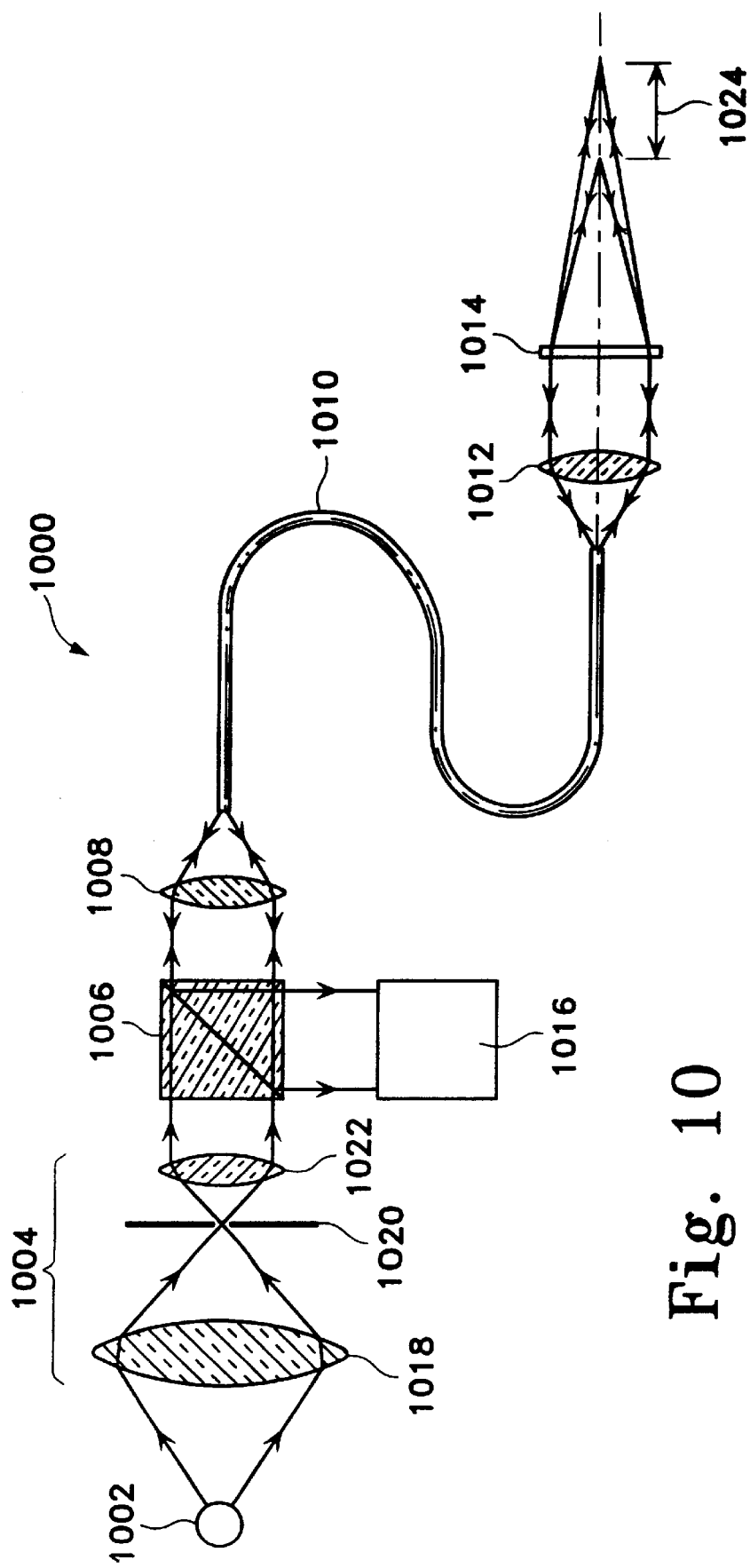
FIG. 10 illustrates a second embodiment of a confocal microscope that employs LCA according to the present invention.

A second embodiment of the present invention is shown in FIG. 10. System 1000 comprises polychromatic light source 1002, input optics 1004, beamsplitter 1006, first objective lens 1008, fiber optic cable 1010, collimator lens 1012, Fresnel zone plate 1014, and spectrometer 1016. Input optics 1004 comprises a first lens 1018, pinhole aperture 1020 and collimator lens 1022.

In operation, system 1000 provides the same basic functioning as the first but employs a few different components. Input optics 1004 projects collimated polychromatic light from light source 1002 onto beamsplitter 1016. First objective lens 1008 focuses the light into fiber optic cable 1010, which provides input light into achromatic collimator lens 1012. Achromatic collimator lens 1012, in turn, projects collimated light without undue chromatic aberration onto Fresnel zone plate 1014.

Zone plate 1014 can be either a diffractive or holographic optical element, as is well known in the art. The function of the zone plate 114 is to provide a known amount of longitudinal chromatic aberration. It will be appreciated that all LCA embodiments of the present invention encompass all means of providing known LCA, including, but not limited to: lenses having known LCA, zone plates, gratings, prisms and the like.

As can be seen in FIG. 10, zone plate 1014 provide a spectral spread 1024, where the focal point of the projected light varies according to wavelength. As with the first embodiment, the wavelength that finds a reflective surface at its focal point is strongly reflected back through zone plate 1014 and lens 1012.

Since lens 1012 focuses these "preferred" wavelengths to the substantially pinhole-size aperture of fiber optic cable 1010, fiber optic cable essentially performs the same function as pinhole aperture 914 in FIG. 9. In fact, wavelengths that are not reflected back from their focal point in spread 1024 are attenuated in the same fashion as with aperture 914. Thus, fiber optic cable 1010 acts as the filter for system 1000. Light emerges from fiber optic cable 1010, is collimated by lens 1008, reflected off beamsplitter 1006, and detected by spectrometer 1016. In the figure, spectrometer 1016 is understood to perform the same function as the lens/grating/spectrometer arrangement of the previous embodiment.

It will be appreciated that the present invention encompasses any other method of providing this filtering effect to provide sharp resolution by wavelength. Thus, the present invention should not be limited only to the embodiments disclosed herein.

A feature of this second embodiment is the use of fiber optic cable 1010. Cable 1010 allows the achromatic collimator lens 1012 and zone plate 1014 to be mobile enough to be employed as a probe. One problem with this fiber optic design is the potential for strong reflection from the probe end of the fiber of the light coming from source 1002. This reflected source light may overpower the return light reflected by the point of interest. This problem may be avoided by employing the third embodiment of the present invention as described below.

THIRD LCA EMBODIMENT

Figure 11:
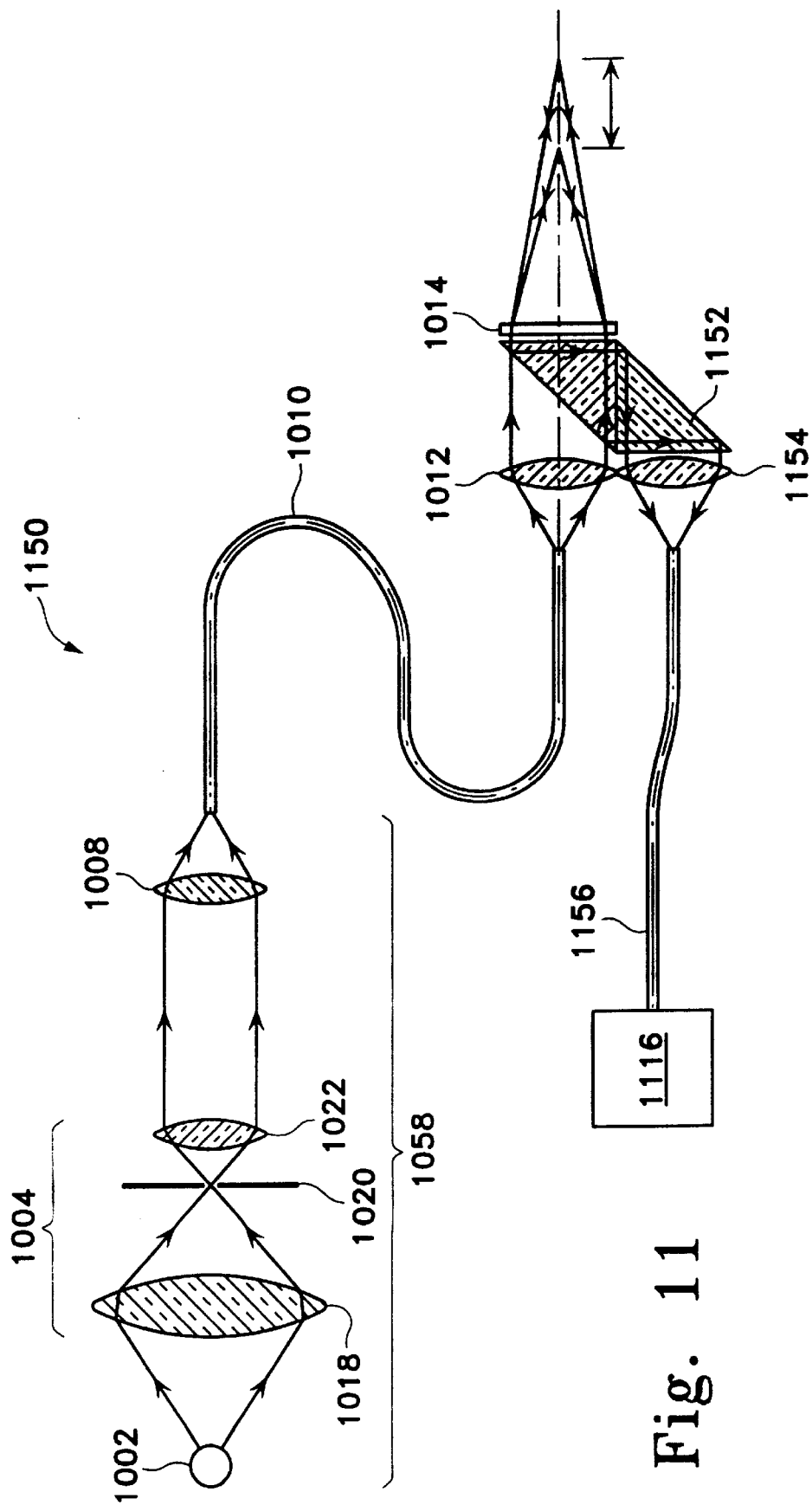
FIG. 11 illustrates a third embodiment of a confocal microscope that employs LCA according to the present invention.

Referring to FIG. 11, a third embodiment 1150 of the present invention is given. The basic idea behind the third embodiment is to provide two separate optical paths—one for the input light from source 1002 and another for the reflected light from the point of interest.

System 1150 has many elements in common with system 100, with like numerals describing like elements. The additional optical elements needed for this embodiment comprise: beamsplitter/translator 1152, second achromatic collimator lens 1154, and second fiber optic cable 1156. As is apparent from FIG. 11, reflected light from the object is split off and translated by beamsplitter/translator 1152 and focused by achromatic collimator lens 1154 into second fiber optic cable 1156, and finally into spectrometer 1116.

It will be appreciated that beamsplitter/translator 1152 could be made from a set of prisms that are contacted and have coatings at the beamsplitting interface. This would maintain alignment much better than the use of a cube splitter and separate mirror, as this element is usually constructed in the art.

FOURTH LCA EMBODIMENT

Figure 12:
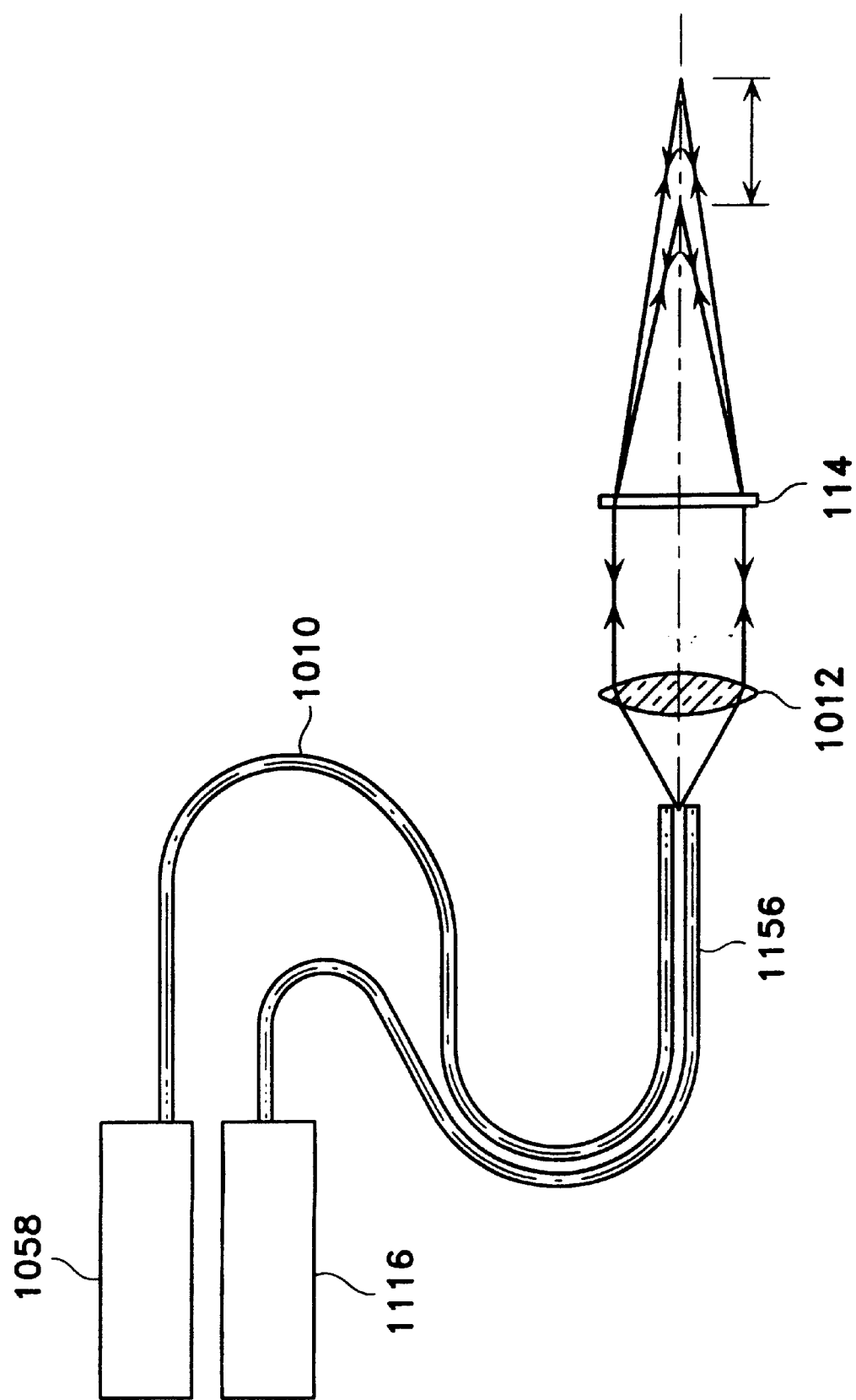
FIG. 12 illustrates a fourth embodiment of a confocal microscope that employs LCA according to the present invention.

A fourth embodiment is shown in FIG. 12 that is similar to the third embodiment given in FIG. 11, with like numerals describing like elements. In this fourth embodiment, again source 1058 and detector 1116 are divided as separate components. The main difference is that the fourth embodiment uses only one collimator lens 1012 instead of two (as provided in FIG. 11). This is accomplished by slightly offsetting both fiber optic cables 1010 and 1156 slightly and symmetrically off-axis.

For all four above-described embodiments, once the present system has detected two wavelengths corresponding to the front surface of the cornea and a second surface from a reflective surface in the cornea respectively, it is necessary to correlate the difference in the respective wavelengths to the actual distances from these two surfaces. As is known in the art, light travelling through any medium other than a vacuum changes its speed based on the medium's refractive index. Thus, the differences in the detected wavelengths must be corrected for the difference in the refractive index of cornea versus air. These calculations are well known to those skilled in the optical arts.

SINGLET AND DOUBLET OPTICAL LENS DESIGNS

As mentioned, the above embodiments may use any number of optical elements that have a known amount of LCA. In particular, two lens systems (i.e., a singlet and a doublet lens system) have been designed to have a known amount of LCA for the purposes of the present invention. Computer simulations have been run to model the wavelength resolution of these lens designs.

The designs of these lens for the present invention differ from lens to be used in conventional confocal microscopy. The fundamental requirement for a conventional confocal system is to have perfect (at least near diffraction limited) imaging on axis over the wavelength band of the source. Often a confocal microscope is used with a monochromatic laser source, suggesting that the system needs only to be optimized for a specific wavelength of light. Thus, a typical scanning confocal microscope is well corrected for color.

For the purposes of the present invention, however, the constraints are different. Near perfect axial imaging is desired but with significant amounts of LCA. Since axial imaging is desired, the dominant aberration that must be considered is spherical aberration.

In a singlet lens system, it is possible to design it so that it has diffraction limited imaging for single wavelengths and a specific pair of object and image locations. However, this is best accomplished with aspheric surfaces. Since LCA is a result of the dispersive property of the material, the selection of the glass type has a direct consequence on the amount of LCA and hence the dynamic range of the instrument. The material should preferably be high index so that spherical aberration varies little with wavelength. A reasonable choice is Schott SF-11, a relatively high index, high dispersion glass that is commonly available.

Figure 13:
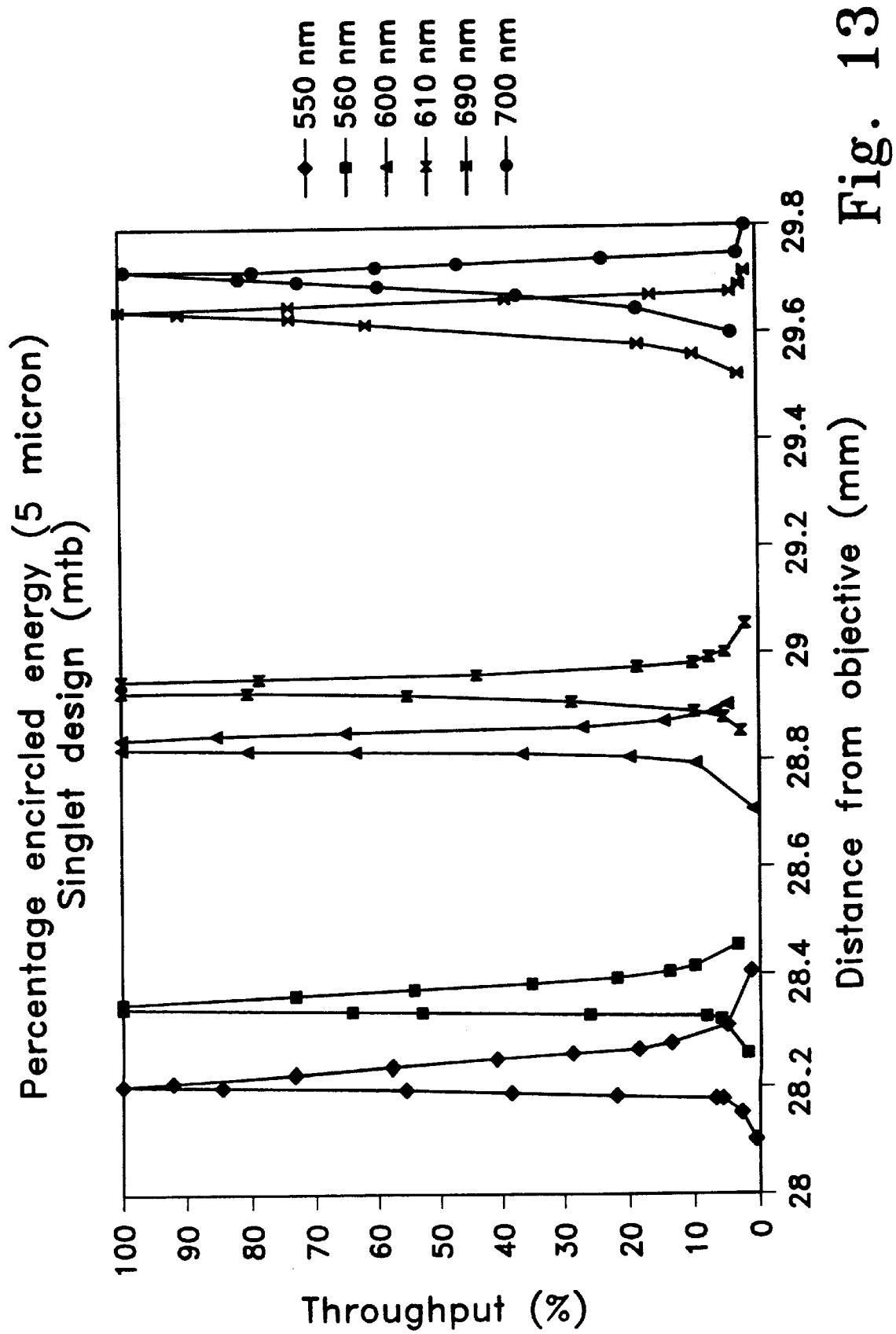
FIG. 13 illustrates the simulated wavelength response of a single lens LCA system.

Based on such an aspheric singlet lens, a computer simulation of a system using the singlet lens was performed. The system is designed to have approximately 1 mm of LCA, operate within a bandwidth of 400–750 nm, and have most of its energy fall within a circle of 5 microns in diameter. FIG. 13 depicts the simulated wavelength response and resolution of such a system.

Each of the six curves in FIG. 13 represents the intensity throughput of a given wavelength reflected by the target surface and picked up at the spectrometer, versus the distance from the objective lens to the target surface. At the point of maximum intensity throughput at the spectrometer, the distance from the objective lens matches the focal point of the particular wavelength. As the distance from the objective lens deviates from the focal point, the intensity of the recorded wavelength would be expected to drop off.

Because the present invention employs a confocal design, the drop-off of intensity throughput is expected to be very dramatic. Thus, resolution of distances would greatly improve. For example in FIG. 13, the two left-most curves represent wavelengths 550 nm and 560 nm respectively. Their maxima occur at approximately 28.22 mm and 28.38 mm–a distance of 0.16 mm apart.

Looking at FIG. 13, several observations can be made. First, at this distance, the maxima are clearly distinguishable (i.e. the curve of one does not subsume the other to the point where one maxima is not visible). Second, the lower bound resolution of the system is potentially much smaller than 0.16 mm. It appears that the distances between maxima could be much closer and still be distinguishable.

An alternative optical design for the purposes of the present invention is a doublet lens system having a known amount of LCA. In typical optical systems, however, doublet lens are constructed to reduce LCA. This is accomplished by using a low dispersion crown glass and a higher dispersion flint glass. For a typical positive doublet, the crown glass is used to make a positive element and a flint is used to make a negative element. The positive element is stronger (i.e. has a shorter focal length) than a singlet of the same combined power. The intent is to produce exactly the same focal length at two wavelengths and much reduced variation over the rest of the useable range.

Figure 14:
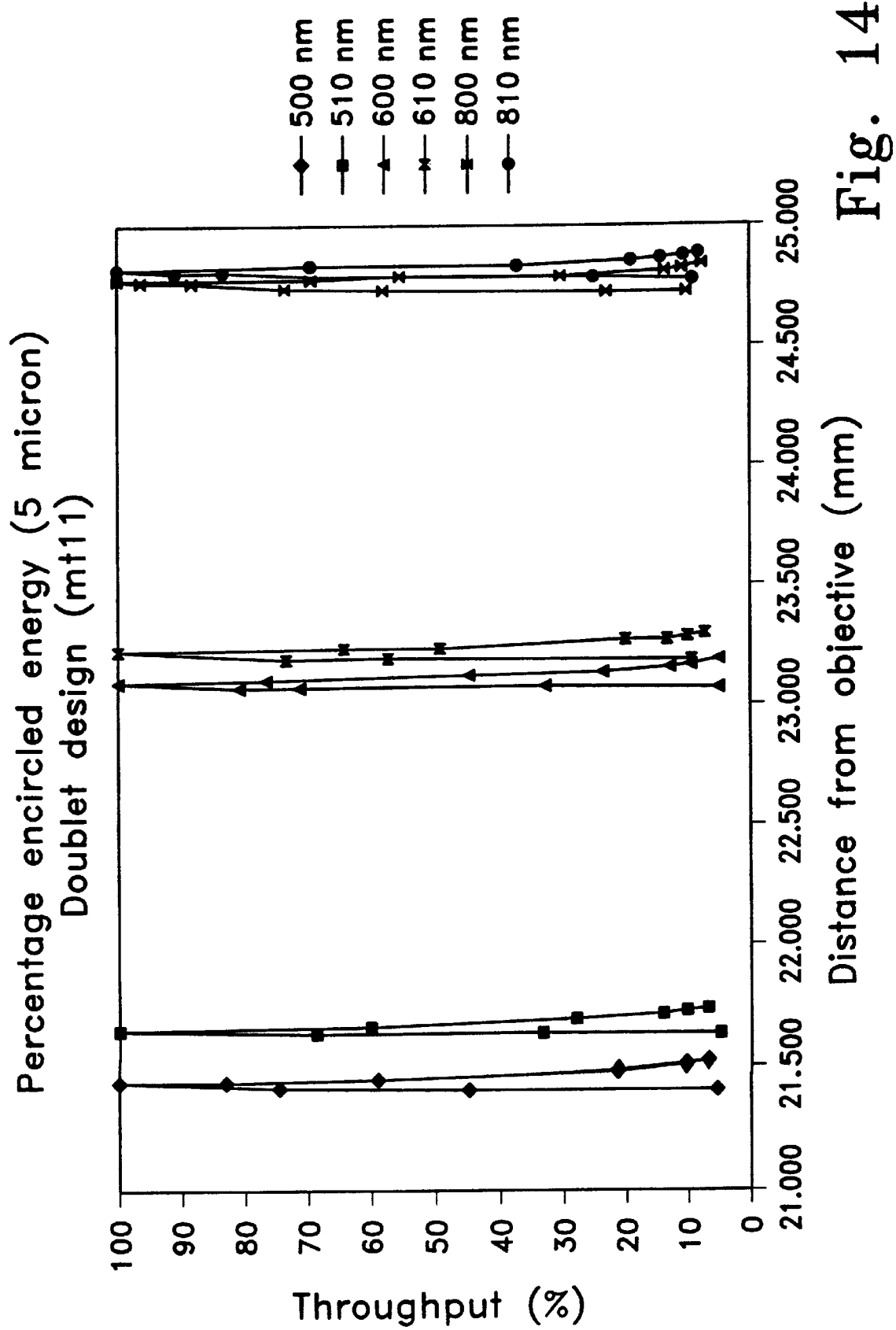
FIG. 14 illustrates the simulated wavelength response of a double lens LCA system.

For the purposes of the present invention, however, even greater LCA is desired than is possible with a singlet. Additionally, it is desired to use spherical surfaces to lower the cost of manufacture. FIG. 14 is a computer simulation of a system employing a series of doublet lenses. As can be seen, the wavelength resolution of the doublet system appears greater than that of the singlet design—with resolution appearing to be about 0.1 mm.

The design of the doublet lenses uses two common glasses (BK7 and SF11) that are placed in a backward fashion to conventional ways of making achromatic doublet lenses. That is, for a positive combination, the negative element is BK7 and the positive element is SF11. The design employs an air space to control spherical aberration rather than producing a cemented design (i.e. where the sides facing each other are essentially the same radius and in contact). The design has a built-in LCA of approximately 3 mm and spherical aberration is well controlled so that most of the energy falls in a circle of 5 microns at the best focus for a given wavelength.

It will be appreciated that this design can be tuned to permit greater of lesser LCA by varying the working distance and F/π. A relatively small F/π can be selected so that depth resolution is good and permit being slightly off-normal and still register accurate measurement.

Although the present invention has been described in conjunction with specific embodiments, it will be appreciated that various modifications and alterations might be made by those skilled in the art without departing from the spirit and scope of the invention.

We claim:

1. A tool for use in determining a measured depth of a tissue pocket having an anterior surface by directing energy toward the pocket from above an anterior surface of the tissue, said tool comprising:

a tool body; and a tool end extending from said tool body and dimensioned to be inserted within the tissue pocket, between layers of tissue formed by an incision, said tool end having a surface defined by length and width dimensions which are adapted to be positioned substantially parallel to the layers of tissue, said tool end further having a thickness dimension smaller than and perpendicular to said length and width dimensions, at least a portion of said tool end characterized by an energy transmission rate which is less than an energy transmission rate of the tissue, wherein said tool end is adapted to reflect the directed energy at a rate slower than the rate of transmission of the directed energy through the tissue wherein the measured depth of the tool below the anterior surface is a function of energy reflected by said tool end.

2. The reflective tool of claim 1, wherein said tool end defines an open space, and said at least a portion of said tool end comprises air contained in the open space.

3. The reflective tool of claim 2, said tool body further comprising a tube communicating with the open space for evacuating fluid from the open space.

4. The reflective tool of claim 1, wherein said at least a portion of said tool end comprises a polymeric layer disposed on said tool end.

5. The reflective tool of claim 4, wherein said polymeric layer comprises a polymer foam layer.

6. The reflective tool of claim 4, where said polymeric layer has a thickness of about 0.003 to 0.020 inches.

7. The reflective tool of claim 1, wherein said at least a portion of said tool end comprises a material having at least one entrapped air space.

8. The reflective tool of claim 1, wherein said at least a portion of said tool end comprises a surface containing one or more air pockets.

9. The reflective tool of claim 1, wherein said at least a portion of said tool end comprises a porous hydrophobic biocompatible material.

10. A tool for insertion into a tissue pocket having an anterior surface and for determining a measured depth of the tissue pocket below the anterior surface by directing energy toward the pocket from above the anterior surface of the tissue, the tool comprising:

a tool body; and a material that is part of the tool body and is configured and dimensioned to slide between layers defining the tissue pocket, said material characterized by an energy transmission rate which is less than an energy transmission rate of tissue defining the tissue pocket, wherein the material in the tissue pocket interacts with the energy, and a measured depth of the tool below the anterior surface is a function of the interaction of the tool and the energy.

11. The tool of claim 10, wherein the material is air.

12. The tool of claim 10, wherein the material is metal.

13. The tool of claim 10, wherein the material is plastic.

14. The tool of claim 10, wherein the energy is ultrasound.

15. The tool of claim 10, wherein the energy is light.

16. The tool of claim 10, wherein the reflective tool is adapted to be inserted into a corneal tissue pocket substantially parallel to the anterior surface of the tissue.

* * * * *